(12) United States Patent
Watkinson et al.

(10) Patent No.: US 6,605,144 B1
(45) Date of Patent: Aug. 12, 2003

(54) HIGH LIGHT- FASTNESS YELLOW COMPOSITION

(75) Inventors: Janette Watkinson, Blackley (GB); John Edward Presgrave, Blackley (GB); Paul Wight, Blackley (GB)

(73) Assignee: Avecia Limited, Blackley (GB)

( * ) Notice: Subject to any disclaimer, the term of this patent is extended or adjusted under 35 U.S.C. 154(b) by 0 days.

(21) Appl. No.: 09/914,018
(22) PCT Filed: Mar. 24, 2000
(86) PCT No.: PCT/GB00/01123
§ 371 (c)(1), (2), (4) Date: Jan. 7, 2002
(87) PCT Pub. No.: WO00/58407
PCT Pub. Date: Oct. 5, 2000

(30) Foreign Application Priority Data

Mar. 30, 1999 (GB) ................................. 9907270

(51) Int. Cl.⁷ ........................ C09D 11/02; C09B 35/03
(52) U.S. Cl. ................ 106/31.48; 106/31.77; 106/496; 8/641
(58) Field of Search ................ 106/31.48, 31.77, 106/496; 8/641; 534/797; 427/466

(56) References Cited

U.S. PATENT DOCUMENTS

| | | | | |
|---|---|---|---|---|
| 4,661,158 A | | 4/1987 | Kobayashi et al. | 106/31.48 |
| 5,374,301 A | | 12/1994 | Gregory et al. | 106/31.48 |
| 5,622,550 A | | 4/1997 | Konishi et al. | 106/31.48 |
| 5,728,201 A | * | 3/1998 | Saito et al. | 106/31.48 |
| 5,749,951 A | * | 5/1998 | Yoshiike et al. | 106/31.27 |
| 5,948,154 A | * | 9/1999 | Hayashi et al. | 106/31.48 |
| 6,342,096 B1 | * | 1/2002 | Kurabayashi | 106/31.27 |
| 6,454,844 B1 | * | 9/2002 | Kanaya | 106/31.48 |
| 6,482,256 B1 | * | 11/2002 | Kanaya et al. | 106/31.51 |

FOREIGN PATENT DOCUMENTS

| | | |
|---|---|---|
| EP | 0 651 037 | 5/1995 |
| WO | WO 98/44053 | 10/1998 |

OTHER PUBLICATIONS

Database WPI, Section Ch, Week 198409, Derwent Publications Ltd., London, GB; Class E21, AN 1984–051532, XP002140405 & JP 59 008775 A (Dainippon Ink & Chem KK) Jan. 18, 1984, abstract.

* cited by examiner

Primary Examiner—Helene Klemanski
(74) Attorney, Agent, or Firm—Pillsbury Winthrop LLP

(57) ABSTRACT

A composition comprising a compound of Formula (1) and compound of Formula (2) or salts thereof:

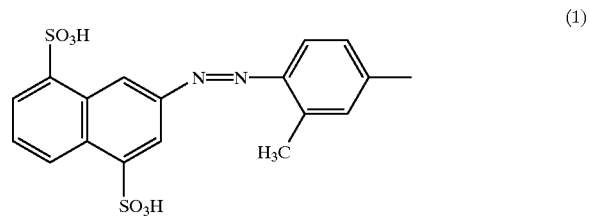

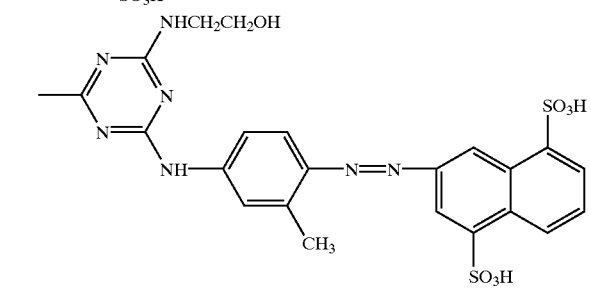

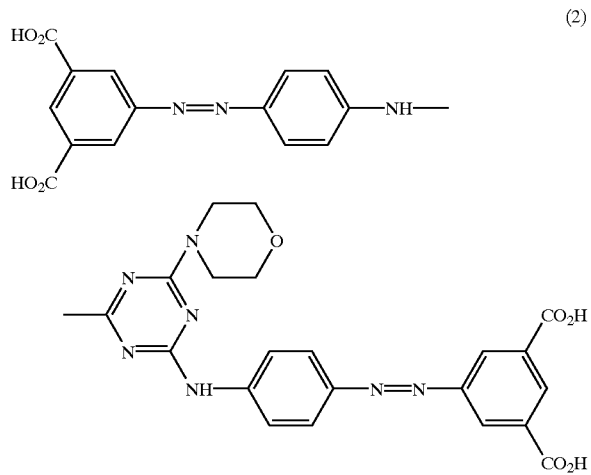

The compositions show good light-fastness and are particularly useful for photorealistic ink jet printing.

13 Claims, No Drawings

HIGH LIGHT- FASTNESS YELLOW COMPOSITION

This application is the National Phase of International Application PCT/GB00/01123 filed Mar. 24, 2000 which designated the United States and that International Application was published under PCT Article 21(2) in English. International Application PCT/GB00/01123 claims priority from Provisional Application 60/144061, filed Jun. 7, 1999, and also claims priority from GB 9907270.4, filed Mar. 30, 1999.

This invention relates to high light-fastness yellow compositions and to their use in ink jet printing ("IJP"). IJP is a non-impact printing technique in which droplets of coloured liquids are ejected through a fine nozzle onto a substrate without bringing the nozzle into contact with the substrate.

IJP is a relatively inexpensive way of recording multi-colour images, for example pictures obtained from digital sources such as electronic cameras, scanners and the Internet. The use of ink jet printers to print colour images in the home or office environment is now becoming commonplace. However IJP has a big disadvantage compared to conventional silver halide photography in that the resultant images fade quite quickly in ordinary daylight. There is a need to improve the light-fastness properties of prints to prevent images vanishing or becoming discoloured over time.

We have now found that a composition comprising two particular yellow dyes defined below in a particular range of ratios has superior light-fastness compared to the individual dyes when printed on commercially available glossy film from Seiko Epson Corporation. The light-fastness is still not as good as for silver halide photographs but the composition does represent a step in the right direction towards improved light-fastness.

According to a first aspect of the present invention there is provided a composition comprising a compound of Formula (1) and compound of Formula (2) or salts thereof:

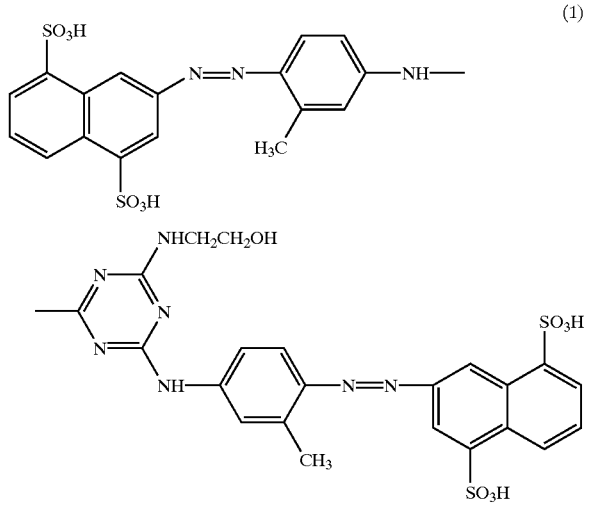

(1)

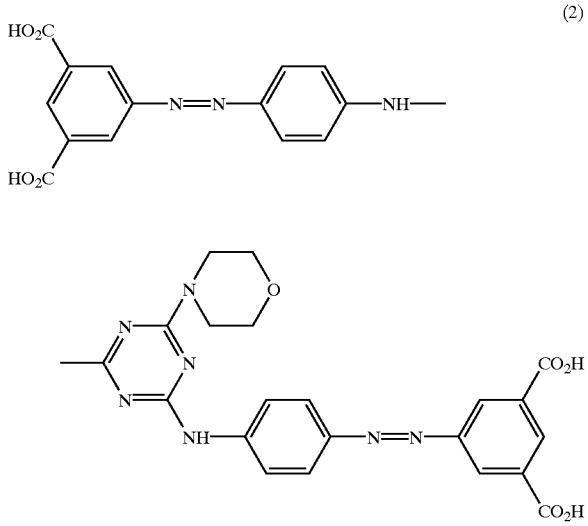

(2)

wherein the weight ratio of the compound of Formula (1) to the compound of Formula (2) is 1:4 to 1:1.

Preferably the weight ratio of the compound of Formula (1) to the compound of Formula (2) is from 1:3.9 to 1:1, more preferably 1:3.5 to 1:1, especially 1:3 to 1:1.

The dye of Formula (1) is known as C.I.Direct Yellow 86 and may be obtained commercially from a number of sources listed in the colour index, including Avecia Limited.

The Dye of Formula (2) may be prepared by the method described in U.S. Pat. No. 5,268,459, Example 6.

Preferred salts are alkali metal salts, especially lithium, sodium and potassium salts, ammonium and substituted ammonium salts. Especially preferred salts are salts with ammonia, an organic amine or a quaternary amine (e.g. $(CH_3)_4N^+$). The dyes may be converted into a salt using known techniques. For example, an alkali metal salt of a dye may be converted into a salt with ammonia or an amine by dissolving an alkali metal salt of the dye in water, acidifying with a mineral acid and adjusting the pH of the solution to pH 9 to 9.5 with ammonia or the amine and removing the alkali metal cations by dialysis.

The dyes may exist in tautomeric forms other than those shown in this specification. These tautomers are included within the scope of the present claims.

According to a second aspect of the present invention there is provided a liquid composition comprising a compound of Formula (1), a compound of Formula (2) and a liquid medium. In a preferred aspect this liquid composition comprises:

(a) from 0.01 to 30 parts of a composition comprising a compound of the Formula (1) and a compound of Formula (2); and (b) from 70 to 99.99 parts of a liquid medium;

wherein all parts are by weight and the number of parts of (a)+(b)=100.

The number of parts of component (a) is preferably from 0.1 to 20, more preferably from 0.5 to 15, and especially from 1 to 5 parts. The number of parts of component (b) is preferably from 99.9 to 80, more preferably from 99.5 to 85, especially from 99 to 95 parts.

The preferred weight ratio of compounds (1) and (2) is as described in relation to the first aspect of the present invention.

Preferably component (a) is completely dissolved in component (b). Preferably component (a) has a solubility in component (b) at 20° C. of at least 10%. This allows the preparation of concentrates which may be used to prepare more dilute inks and reduces the chance of the dye precipitating if evaporation of the liquid medium occurs during storage.

Preferred liquid media include water, a mixture of water and an organic solvent and an organic solvent free from water.

When the liquid medium comprises a mixture of water and an organic solvent, the weight ratio of water to organic solvent is preferably from 99:1 to 1:99, more preferably from 99:1 to 50:50 and especially from 95:5 to 80:20.

It is preferred that the organic solvent present in the mixture of water and organic solvent is a water-miscible organic solvent or a mixture of such solvents. Preferred water-miscible organic solvents include $C_{1-6}$-alkanols, preferably methanol, ethanol, n-propanol, isopropanol, n-butanol, sec-butanol, tert-butanol, n-pentanol, cyclopentanol and cyclohexanol; linear amides, preferably dimethylformamide or dimethylacetamide; ketones and ketone-alcohols, preferably acetone, methyl ether ketone, cyclohexanone and diacetone alcohol; water-miscible ethers, preferably tetrahydrofuran and dioxane; diols, preferably diols having from 2 to 12 carbon atoms, for example pentane-1,5-diol, ethylene glycol, propylene glycol, butylene glycol, pentylene glycol, hexylene glycol and thiodiglycol and oligo- and poly-alkyleneglycols, preferably diethylene glycol, triethylene glycol, polyethylene glycol and polypropylene glycol; triols, preferably glycerol and 1,2,6-hexanetriol; mono-$C_{1-4}$-alkyl ethers of diols, preferably mono-$C_{1-4}$-alkyl ethers of diols having 2 to 12 carbon atoms, especially 2-methoxyethanol, 2-(2-methoxyethoxy)ethanol, 2-(2-ethoxyethoxy)-ethanol, 2-[2-(2-methoxyethoxy)ethoxy]ethanol, 2-[2-(2-ethoxyethoxy)-ethoxy]-ethanol and ethyleneglycol monoallylether; cyclic amides, preferably 2-pyrrolidone, N-methyl-2-pyrrolidone, N-ethyl-2-pyrrolidone, caprolactam and 1,3-dimethylimidazolidone; cyclic esters, preferably caprolactone; sulphoxides, preferably dimethyl sulphoxide and sulpholane. Preferably the liquid medium comprises water and 2 or more, especially from 2 to 8, water-soluble organic solvents.

Examples of further suitable ink media comprising a mixture of water and one or more organic solvents are described in U.S. Pat. No. 4,963,189, U.S. Pat. No. 4,703,113, U.S. Pat. No. 4,626,284 and EP 4,251,50A.

When the liquid medium comprises an organic solvent free from water, (i.e. less than 1% water by weight) the solvent preferably has a boiling point of from 30° to 200° C., more preferably of from 40° to 150° C., especially from 50 to 125° C. The organic solvent may be water-immiscible, water-miscible or a mixture of such solvents. Preferred water-miscible organic solvents are any of the hereinbefore described water-miscible organic solvents and mixtures thereof. Preferred water-immiscible solvents include, for example, aliphatic hydrocarbons; esters, preferably ethyl acetate; chlorinated hydrocarbons, preferably $CH_2Cl_2$; and ethers, preferably diethyl ether; and mixtures thereof.

When the liquid medium comprises a water-immiscible organic solvent, preferably a polar solvent is included because this enhances solubility of the dye in the liquid medium. Examples of polar solvents include $C_{1-4}$-alcohols. In view of the foregoing preferences it is especially preferred that where the liquid medium is an organic solvent free from water it comprises a ketone (especially methyl ethyl ketone) &/or an alcohol (especially a $C_{1-4}$-alkanol, more especially ethanol or propanol).

The organic solvent free from water may be a single organic solvent or a mixture of two or more organic solvents. It is preferred that when the medium is an organic solvent free from water it is a mixture of 2 to 5 different organic solvents. This allows a medium to be selected which gives good control over the drying characteristics and storage stability of the ink.

When the liquid medium is an organic solvent free from water the compounds of Formula (1) and (2) are preferably in the form of a salt with a lipophilic amine.

Liquid compositions in which component (b) is an organic solvent free from water are particularly useful where fast drying times are required and particularly when printing onto hydrophobic and non-absorbent substrates, for example plastics, metal and glass.

The composition may also contain additional components conventionally used in ink jet printing inks, for example viscosity and surface tension modifiers, corrosion inhibitors, biocides (e.g. Proxel from Avecia Ltd), kogation reducing additives and surfactants which may be ionic or non-ionic.

Preferably the liquid composition has been filtered through a filter having a mean pore size below 10 $\mu$m, more preferably below 5 $\mu$m, especially below 2 $\mu$m, more especially below 1 $\mu$m. In this way particulate matter is removed which could otherwise block the fine nozzles used in ink jet printers.

Preferably the liquid composition has a viscosity of below 20 cp, more preferably below 10 cp, especially below 5 cp, at 20° C.

Preferably the compounds of Formula (1) and (2) are purified by reverse osmosis, ultrafiltration, ion exchange or a combination thereof, either before or after they are incorporated in a composition according to the present invention.

The liquid compositions of the present invention are surprisingly superior for printing images on glossy media from Seiko Epson compared to compositions containing only one of the compounds and to compositions having different ratios of the dyes.

Preferably the liquid composition is yellow.

A further aspect of the invention provides a process for printing a high light-fastness image on a substrate comprising applying thereto a liquid composition according to the second aspect of the present invention by means of an ink jet printer.

The ink jet printer preferably applies the composition to the substrate in the form of droplets which are ejected through a small orifice onto the substrate. Preferred ink jet printers are piezoelectric ink jet printers and thermal ink jet printers. In thermal ink jet printers, programmed pulses of heat are applied to the composition in a reservoir by means of a resistor adjacent to the orifice, thereby causing the composition to be ejected in the form of small droplets directed towards the substrate during relative movement between the substrate and the orifice. In piezoelectric ink jet printers the oscillation of a small crystal causes ejection of the composition from the orifice.

The substrate is preferably a glossy film, especially a glossy film from Seiko Epson Corporation.

A further aspect of the present invention provides a glossy paper, printed with composition as hereinbefore defined.

A still further aspect of the invention provides an ink jet printer cartridge, optionally refillable, containing a liquid composition according to the present invention.

The invention is further illustrated by the following Examples in which all parts, percentages and ratios are by weight unless otherwise stated.

EXAMPLE 1

Inks were prepared by dissolving 0.4 g of dye mixture in a mixture of water (7.5 g), butyl carbitol (1 g), glycerol (1 g) and Surfynol™ 465 (0.1 g) by sonication. The pH was adjusted to 9.5 using NaOH. The resultant mixtures were filtered through a 0.45 µM filter and the resultant inks were put into one chamber of a SEC trichamber ink jet printer cartridge. The dye mixtures contained the various ratios of Dye 2:Dye 1 shown in Table 1 below. These inks were placed in the ink jet printer cartridge and the cartridge loaded into an SEC Stylus Pro ink jet printer. The inks were printed onto SEC glossy film ("SGF"). When dry a portion of each print was mounted, half covered, in an Atlas Ci35a weatherometer and irradiated for 50 hours. The print was removed and the light fastness, determined by the ΔE (colour difference) between the irradiated and un-irradiated portion measured using an X-Rite 938 spectrodensitometer. A lower figure for ΔE indicates higher light fastness.

The humidity fastness of the sample was checked by exposing the print to a humid atmosphere at 60° C. for 16 hours and awarding a rating between 1 and 5 (where 5=very good and 1 is bad).

The results are shown in Table 1 below wherein L, a, b refer to the colour co-ordinates, C is chroma, H is hue and ROD is the optical density of the print. DY132 is C.I.Direct Yellow 132 (a comparative example).

TABLE 1

| Ratio Dye 2:Dye 1 | Substrate | ROD | L | A | B | C | H | ΔE 50 HRS |
|---|---|---|---|---|---|---|---|---|
| Dye 2 (alone) | SGF | 0.945 | 90 | −11 | 96 | 96 | 96 | 11 |
| Dye 1 (alone) | SGF | 1.683 | 82 | 13 | 115 | 116 | 83 | 9 |
| DY132 (alone) | SGF | 1.347 | 87 | −4 | 114 | 114 | 92 | 10 |
| 1/1 | SGF | 1.362 | 86 | 2 | 112 | 112 | 89 | 4 |
| 1.25/1 | SGF | 1.354 | 86 | 1 | 112 | 112 | 89 | 3 |
| 1.5/1 | SGF | 1.295 | 87 | 0 | 110 | 110 | 90 | 4 |
| 1.75/1 | SGF | 1.257 | 87 | −2 | 109 | 109 | 91 | 4 |
| 2.0/1 | SGF | 1.248 | 87 | −2 | 109 | 109 | 91 | 4 |
| 3.0/1 | SGF | 1.142 | 88 | −4 | 105 | 105 | 92 | 5 |
| 4.0/1 | SGF | 1.129 | 89 | −6 | 105 | 105 | 93 | 9 |
| 5.0/1 | SGF | 1.09 | 89 | −7 | 104 | 104 | 94 | 9 |

EXAMPLE 2

Further Inks

The inks described in Tables 2 and 3 may be prepared wherein the composition described in the first column describes the ratio of Dye 1:Dye 2. Numbers quoted in the second column onwards refer to the number of parts of the relevant ingredient and all parts and ratios are by weight. The inks may be applied to paper by thermal or piezo ink jet printing.

The following abbreviations are used in Tables 1 to 3:

PG=propylene glycol
DEG=diethylene glycol
NMP=N-methyl pyrollidone
DMK=dimethylketone
IPA=isopropanol
MEOH=methanol
2P=2-pyrollidone
MIBK=methylisobutyl ketone
P12=propane-1,2-diol
BDL=butane-2,3-diol
CET=cetyl ammonium bromide
PHO=$Na_2HPO_4$ and
TBT=tertiary butanol
TDG=urea

TABLE 2

| Ratio Dye 1:Dye 2 | Dye Content | Water | PG | DEG | NMP | DMK | NaOH | Na Stearate | IPA | MEOH | 2P | MIBK |
|---|---|---|---|---|---|---|---|---|---|---|---|---|
| 1:2 | 2.0 | 80 | 5 | | 6 | 4 | | | | | 5 | |
| 1:3 | 3.0 | 90 | | 5 | 5 | | 0.2 | | | | | |
| 1:1 | 10.0 | 85 | 3 | | 3 | 3 | | | | 5 | 1 | |
| 1:4 | 2.1 | 91 | | 8 | | | | | | | | 1 |
| 1:2.5 | 1.1 | 81 | | | 9 | | 0.5 | 0.5 | | | 9 | |
| 1:2 | 2.5 | 60 | 4 | 15 | 3 | 3 | | | 6 | 10 | 5 | 4 |
| 1:3 | 5 | 65 | | 20 | | | | | 10 | | | |
| 1:4 | 2.4 | 75 | 5 | 4 | | 5 | | | | 6 | | 5 |
| 1:1 | 3.2 | 65 | | 5 | 4 | 6 | | | 5 | 4 | 6 | 5 |
| 1:4 | 10.0 | 80 | 2 | 6 | 2 | 5 | | | | | 4 | |
| 1:2 | 1.8 | 80 | | 5 | | | | | 1 | | 15 | |
| 1:3.5 | 2.6 | 84 | | | 11 | | | | | | 5 | |
| 1:2 | 3.3 | 80 | 2 | | | 10 | | | | 2 | | 6 |
| 1:2 | 12.0 | 90 | | | | 7 | | | | | | |
| 1:3 | 5.4 | 69 | 2 | 20 | 2 | 1 | 0.3 | | 3 | | 3 | 3 |
| 1:3 | 6.0 | 91 | | | 4 | | | | | | 5 | |

TABLE 3

| Ratio Dye 1:Dye 2 | Composition Content | Water | PG | DEG | NMP | CET | TBT | TDG | BDL | PHO | 2P | PI2 |
|---|---|---|---|---|---|---|---|---|---|---|---|---|
| 1:2 | 2.5 | 90 | | 6 | 4 | | | | | 0.12 | | |
| 1:1.8 | 3.1 | 82 | 4 | 8 | | 0.3 | | | | | | 6 |
| 1:2.2 | 0.9 | 85 | | 10 | | | | | 5 | 0.2 | | |
| 1:3 | 8.0 | 90 | | 5 | 5 | | | 0.3 | | | | |
| 1:3.1 | 4.0 | 70 | | 10 | 4 | | | | 1 | | 4 | 11 |
| 1:3 | 2.2 | 75 | 4 | 10 | 3 | | | | 2 | | 6 | |
| 1:2.5 | 10.0 | 91 | | | 6 | | | | | | 3 | |
| 1:1 | 9.0 | 76 | | 9 | 7 | | 3.0 | | | 0.95 | 5 | |
| 1:4 | 2.1 | 70 | 5 | 5 | 5 | 0.1 | 0.2 | 0.1 | 5 | 0.1 | 5 | |
| 1:3 | 2.0 | 90 | | | 10 | | | | | | | |
| 1:3 | 2 | 88 | | | | | | 10 | | | | |
| 1:3 | 5 | 78 | | | 5 | | | 12 | | | 5 | |
| 1:3.5 | 8 | 70 | 2 | | 8 | | | 15 | | | 5 | |
| 1:2 | 10 | 80 | | | | | | 8 | | | 12 | |
| 1:2.5 | 10 | 80 | | | 10 | | | | | | | |

What is claimed is:

1. A composition comprising a compound of Formula (1) and compound of Formula (2) or salts thereof:

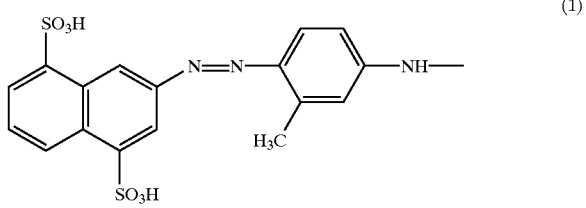

(1)

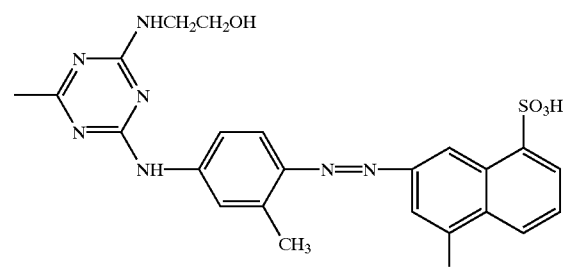

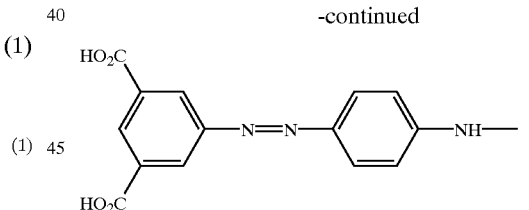

(2)

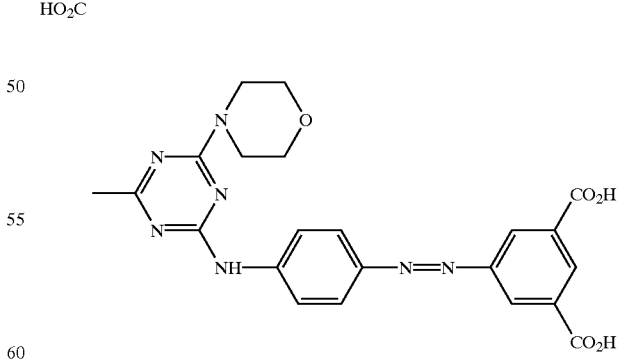

wherein the weight ratio of the compound of Formula (1) to the compound of Formula (2) is 1:4 to 1:1.

2. A composition according to claim 1 wherein the weight ratio of the compound of Formula (1) to the compound of Formula (2) is from 1:3 to 1:1.

3. A liquid composition comprising a composition according to claims 1 or 2 and a liquid medium.

4. A liquid composition which comprises:
(a) from 0.01 to 30 parts of the composition according to claim 1 or 2; and
(b) from 70 to 99.99 parts of a liquid medium.

5. A liquid composition according to claim 3 wherein the liquid medium comprises a mixture of water and an organic solvent.

6. A liquid composition according to claim 4 which has been filtered through a filter having a mean pore size below 10 μm.

7. A liquid composition according to claim 4 having a viscosity below 20 cp at 20° C.

8. A composition according to claim 1 wherein the compounds of Formula (1) and (2) are purified by reverse osmosis, ultrafiltration, ion exchange or a combination thereof, either before or after preparation of the composition.

9. A liquid composition according to claim 4 which is yellow.

10. A process for printing a high light-fastness image on a substrate comprising applying thereto a composition according to claim 4.

11. A process according to claim 10 wherein the substrate is a glossy film.

12. An ink jet printer cartridge, optionally refillable, containing a composition according to claim 1.

13. An ink jet printer containing a liquid composition according to claim 4.

* * * * *

UNITED STATES PATENT AND TRADEMARK OFFICE
CERTIFICATE OF CORRECTION

PATENT NO.     : 6,605,144 B1                                              Page 1 of 1
DATED          : August 12, 2003
INVENTOR(S)    : Watkinson et al.

It is certified that error appears in the above-identified patent and that said Letters Patent is hereby corrected as shown below:

<u>Title page,</u>
Please insert the following:
-- Related U.S. Application Data
[60]    Provisional application No. 60/144,061, filed on July 16, 1999. --

Signed and Sealed this

Thirtieth Day of December, 2003

JAMES E. ROGAN
*Director of the United States Patent and Trademark Office*